United States Patent [19]

Hackett

[11] 4,453,424
[45] Jun. 12, 1984

[54] MOLTEN METAL SAMPLER

[75] Inventor: Robert J. Hackett, Brookfield, Conn.

[73] Assignee: Haly, Inc., Brookfield, Conn.

[21] Appl. No.: 445,002

[22] Filed: Nov. 29, 1982

Related U.S. Application Data

[63] Continuation-in-part of Ser. No. 258,873, Apr. 29, 1981, abandoned.

[51] Int. Cl.³ .............................................. G01N 1/12
[52] U.S. Cl. ............................... 73/864.58; 73/864.59
[58] Field of Search .......... 73/864.53, 864.54, 864.55, 73/864.56, 864.57, 864.58, 864.59, DIG. 9

[56] References Cited

U.S. PATENT DOCUMENTS

| 3,859,857 | 1/1975 | Falk | 73/864.59 |
| 4,002,072 | 1/1977 | Collins | 73/864.56 |
| 4,007,641 | 2/1977 | Kelsey | 73/864.55 |
| 4,046,016 | 9/1977 | Hacket | 73/864.57 |
| 4,211,117 | 7/1980 | Cure | 73/864.55 |

Primary Examiner—S. Clement Swisher

Attorney, Agent, or Firm—Mattern, Ware, Stoltz & Fressola

[57] ABSTRACT

A portable elongated sampler assembly for molten metals incorporates a long, open-ended heat-insulated lance tube carrying, removably telescoped in its open distal end and protruding therefrom, a hollow cylindrical chill mold tube sampler, and a longitudinally reciprocable ejector hammer assembly extends inside the opposite proximal end of the lance tube. Upon actuation, the ejector hammer impacts the telescoped end of the sampler, ejecting it from the lance tube. The sampler preferably includes a ceramic chill mold tube embraced in a hinged, detachable hollow riser vent conducting air displaced by molten metal from the sampler through vent slots to the atmosphere, and the entrance portal of the chill mold tube is closed by a sheet metal cap having an exterior paper slag-cover thereon. Metal deoxidant in wire coil form is embraced between the cap and the entrance portal of the chill mold tube. A fluted copper crown cap without deoxidant may be cemented over the entrance portal of the chill mold tube to form a low temperature sampler for galvanizing baths of molten zinc.

11 Claims, 11 Drawing Figures

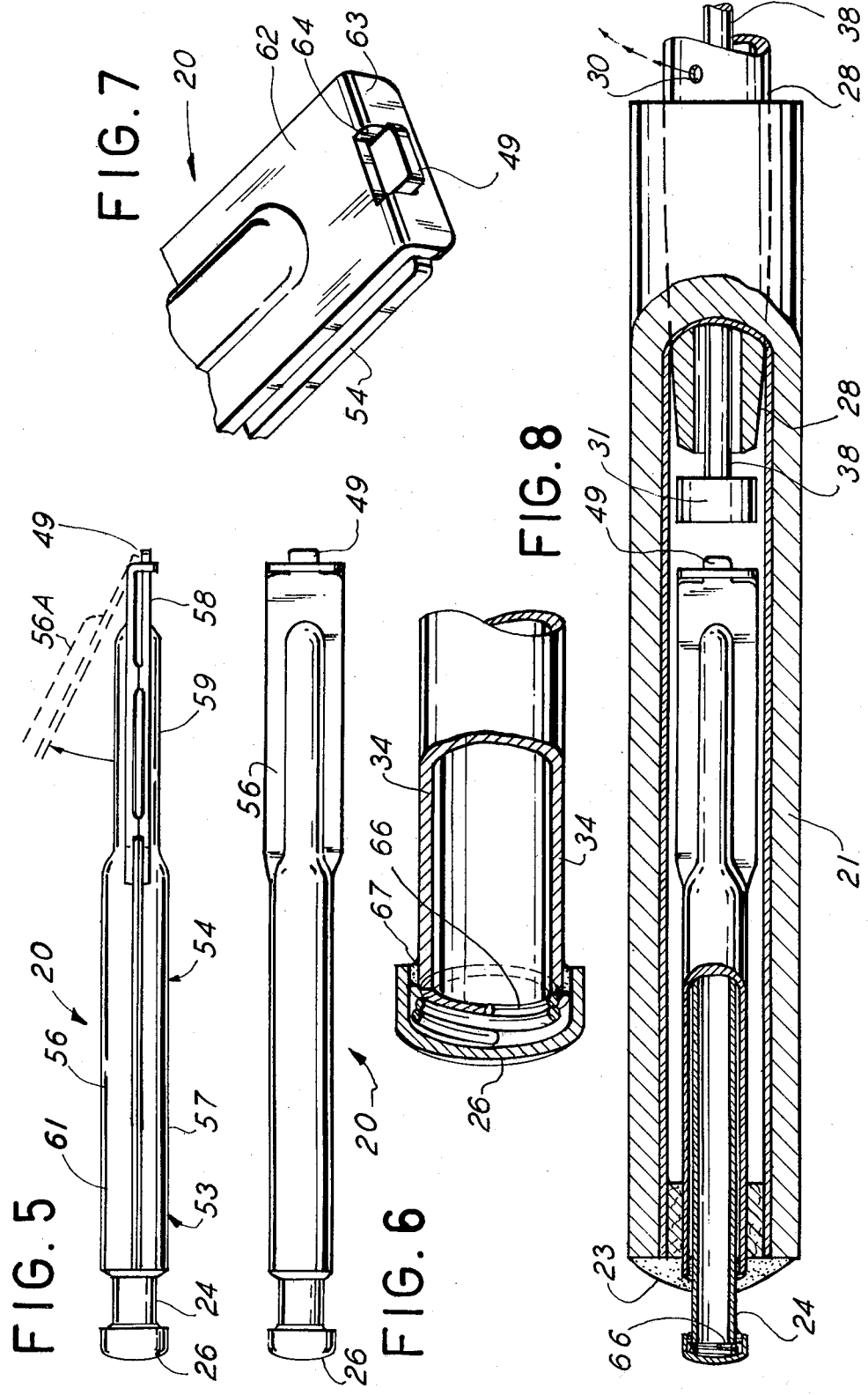

MOLTEN METAL SAMPLER

CROSS REFERENCE TO RELATED APPLICATION

This application is a continuation-in-part of my copending U.S. patent application Ser. No. 258,873, filed Apr. 29, 1981 now abandoned.

This invention relates to samplers for determining the metallurgical composition of molten metals, by withdrawing small samples directly from the melt in a sampler designed to chill and deliver the solidified sample for immediate metallurgical analysis, and particularly to rapid chilling samplers combined with a sample-carrying ejector lance assembly capable of deploying the sampler beneath the liquid surface of the melt, withdrawing it therefrom and immediately dispensing the sampler by ejecting it from the lance into a chilling bath such as liquid nitrogen or ice water in order to minimize diffusion of highly volatile component gases from the sample.

BACKGROUND ART

Conventional spoon or ladle samplers for collecting samples of molten metal to be solidified and tested for metallurgical composition and properties have now largely been supplanted by small, specially designed sampler molds of glass, ceramic or sheet steel, encased in protective insulating material such as multiple layers of paper or the foamed ceramic insulating material described in my U.S. Pat. No. 3,561,494. These small samplers are carried at the remote end of tubular steel lances which are likewise enclosed in protective insulating material in the manner illustrated in my U.S. Pat. Nos. 3,452,602, 3,686,949 and 4,046,016. These sampler molds are provided with inlet ports closed by a thin protective paper-covered cap of sheet metal cemented in place, and the metal cap closely matches the composition of the melt to be sampled. Upon immersion beneath the surface of the melt, the sheet metal caps are quickly melted and the fluid static pressure of molten metal drives the melt through the immersed inlet port into the interior of the sampler mold, displacing air therefrom through suitable escape vents until the mold is completely filled with molten metal. Being much colder than the melt, the mold withdraws heat from the molten metal inside it, reducing its temperature and causing the sample to solidify inside the mold.

For most metallurgical constituents of normal melt compositions, the operation of these small sampler molds is highly satisfactory. For determination of the constituent percentages of gaseous components having extremely small molecular weights which diffuse rapidly from the solidifying metal, however, these samplers have proved inadequate, since the solidified sample contains only a small proportion of the rapidly diffusing low molecular weight gases such as hydrogen.

Accordingly, complex and expensive sampling and estimating techniques have proved necessary in order to secure even approximate estimates of the percentage of such low molecular weight gases in molten metal compositions.

Maximum hydrogen percentages normally do not exceed two parts per million, making accurate sampling and analysis procedures highly critical.

Currently accepted practice for obtaining molten metal samples for hydrogen analysis involve a large metal spoon which is first coated with slag by dipping it into the melt. Then the spoon is redipped beneath the floating slag layer to a deeper depth within the melt filling the interior of the slag coated spoon with molten metal. The spoon is then withdrawn from the melt and set on the plant floor. An evacuated glass pin sampler mold tube held in a pair of tongs normally manipulated by a second operator is then dipped into the molten metal held in the spoon. The tip of the evacuated glass tube melts off and the vacuum draws the molten metal up inside the tube. Such an evacuated glass tube or tongs cannot be exposed to the normal high melt temperatures inside a furnace because they could not be retrieved before they would melt. Hence the intermediate spoon sampling is a necessity.

During all such procedures, hydrogen is rapidly diffusing from the molten metal held in the spoon, drastically affecting the accuracy of any hydrogen percentage determined by analysis of the sample eventually drawn inside the evaluated glass tube. In addition, the molten metal drawn inside the evacuated glass tube is free to drain out again because there is no chilling means solidifying the molten sample. Because of the vulnerability of the evacuated glass tube sampler, there is no way to take samples directly from a furnace or large ladle and the intermediate sampling spoon procedure cannot be avoided; in addition, there is no way to take samples through a floating slag layer whose high temperature will melt the glass tube before it is immersed through the floating slag.

For all of these reasons, determination of the hydrogen content of molten metal has been extremely difficult or impossible.

DISCLOSURE OF THE INVENTION

The molten metal samplers and lance assemblies of the present invention provide an efficient and relatively inexpensive solution to these difficult problems. The small compact samplers characterizing this invention in their enclosing tubular casings produce pin samples admirably suited for analysis by spectrographic and spectrophotometric techniques. The sampler casing is also designed to absorb the blow of an internal ejector hammer incorporated in the lance assembly, carrying the sampler and the enclosed sample into a low temperature liquid bath for rapid chilling. In addition, the lance assemblies of this invention are provided with a powerful but easily operated ejector hammer assembly which can be armed or cocked by the sampler operator before immersion of the sampler in the melt, and then quickly actuated to eject the sample and the sampler into the low temperature chilling bath, with the ejector lance assembly being ready for immediate reloading with a new sampler and casing, ready for the next sampling operation.

Accordingly, a principal object of the present invention is to provide an efficient and inexpensive molten metal sampler and ejector lance assembly easily loaded and cocked to prepare for a sampling operation, which may be actuated quickly to eject the sampler for rapid chilling of the molten metal sample.

Another object of the invention is to provide convenient and effective ejector lances, capable of carrying a small compact molten metal sampler of this invention for immersion beneath the surface of the melt, and capable of ejecting the filled sampler immediately into a low temperature fluid bath for rapid chilling.

Still another object of the invention is to provide small compact molten samplers in protective enclosure casings capable of producing lightweight pin samples for metallurgical analysis while also being capable of withstanding the physical shock of ejection from the ejector lance and the thermal shock of sudden immersion in low temperature fluid chilling baths.

A further object of the invention is to provide deoxidizing techniques for miniature "pin-samplers", permitting rapid accurate sampling and avoiding collecting, handling and chilling unneeded volumes of sampled metal from the melt.

Still another object of the invention is to provide samplers for lower temperature molten metal baths of zinc or aluminum using a fluted cap of metal of a higher melting temperature.

Other objects of the invention will in part be obvious and will in part appear hereinafter.

The invention accordingly comprises the features of construction, combinations of elements, and arrangement of parts which will be exemplified in the constructions hereinafter set forth, and the scope of the invention will be indicated in the claims.

For a fuller understanding of the nature and objects of the invention, reference should be had to the following detailed description taken in connection with the accompanying drawings.

THE DRAWINGS

FIG. 4 is a greatly enlarged fragmentary cross-sectional top plan view of the molten metal sampler installed in the remote end of the lance assembly with the ejector hammer in its cocked or armed position, ready for ejector actuation;

FIG. 5 is a similar side elevation view of a compact molten metal pin sampler of the present invention encased in its protective casing;

FIG. 6 is a top plan view of the same molten metal sampler and its protective casing shown in FIG. 5;

FIG. 7 is a further enlarged fragmentary perspective view of the proximal end of the sampler casing showing the latching interfitting assembly of its two vent plates, ready to receive the ejecting blow from the ejector hammer;

FIG. 8 is a greatly enlarged fragmentary side elevation view, partially in section, showing the inlet portal of the molten metal sampler characterizing the present invention, closed by its protective cover and incorporating a coiled length of deoxidizing wire secured directly around the inlet portal;

BEST MODE FOR CARRYING OUT THE INVENTION

Figure 1:
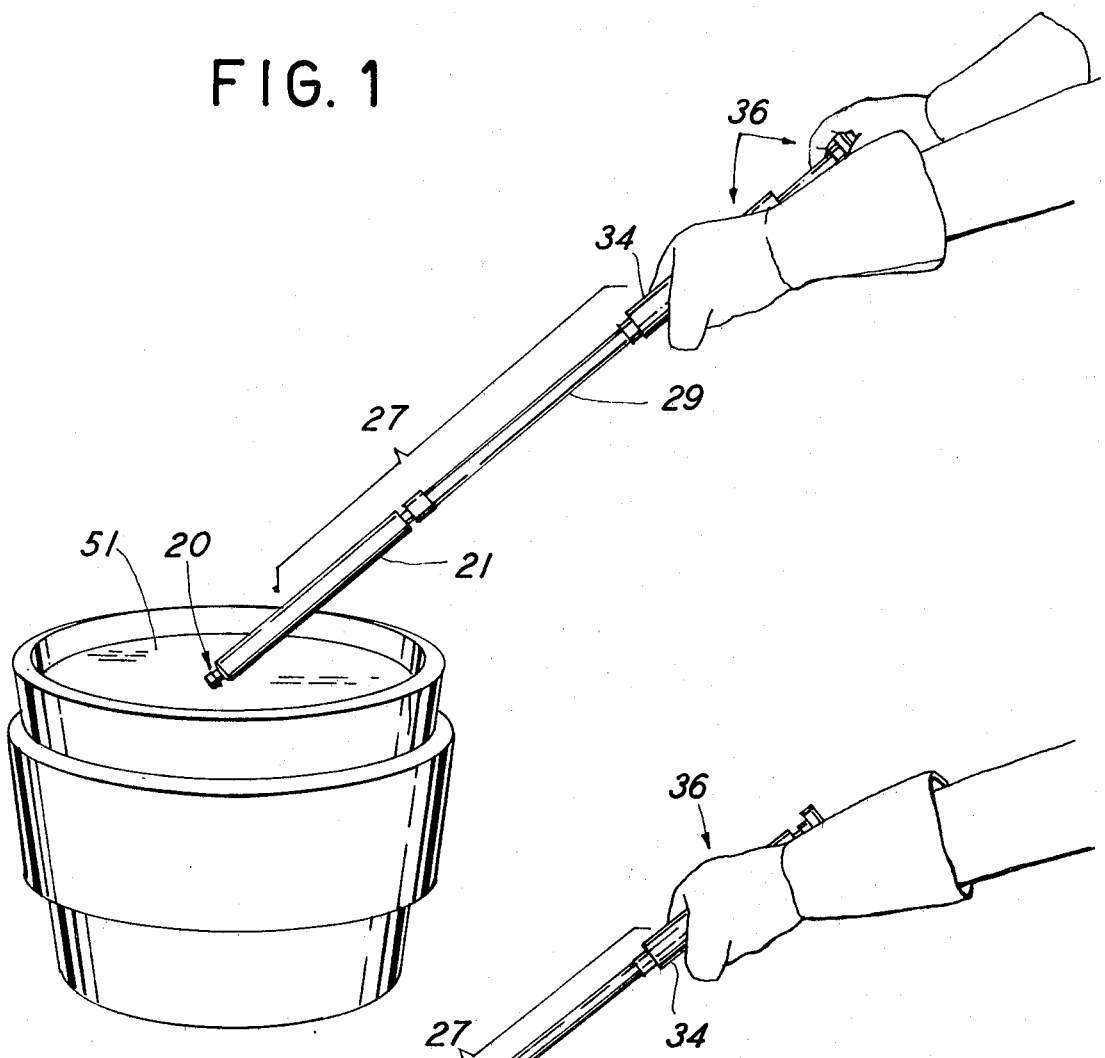
FIG. 1 is an overall perspective view of the sampler and ejector lance assembly of the present invention being inserted by the operator into the melt.
Figure 2:
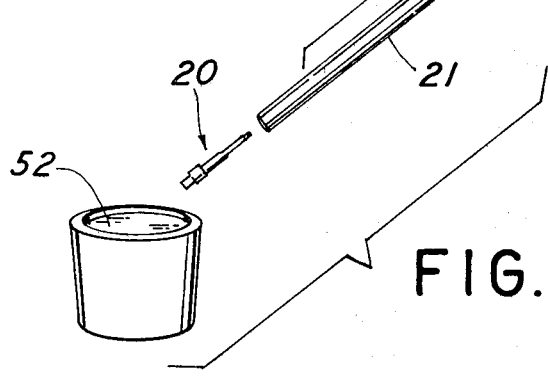
FIG. 2 is a comparable perspective view of the same assembly, after it has been actuated by the operator, with the sampler ejected and travelling toward the chilling bath.

The molten metal samplers and ejector lance assemblies of the present invention provide efficient, easily operated and relatively inexpensive devices for securing highly reliable metallurgical samples of molten metal from the melt in unusually quick sampling operations. The two successive steps employed in each of these sampling operations are illustrated in FIGS. 1 and 2, where the initial sample collection step is illustrated with the sampler being immersed in the melt in FIG. 1, and the sample ejection step for quick chilling of the sample in a low temperature fluid bath is shown in FIG. 2.

Figure 3:
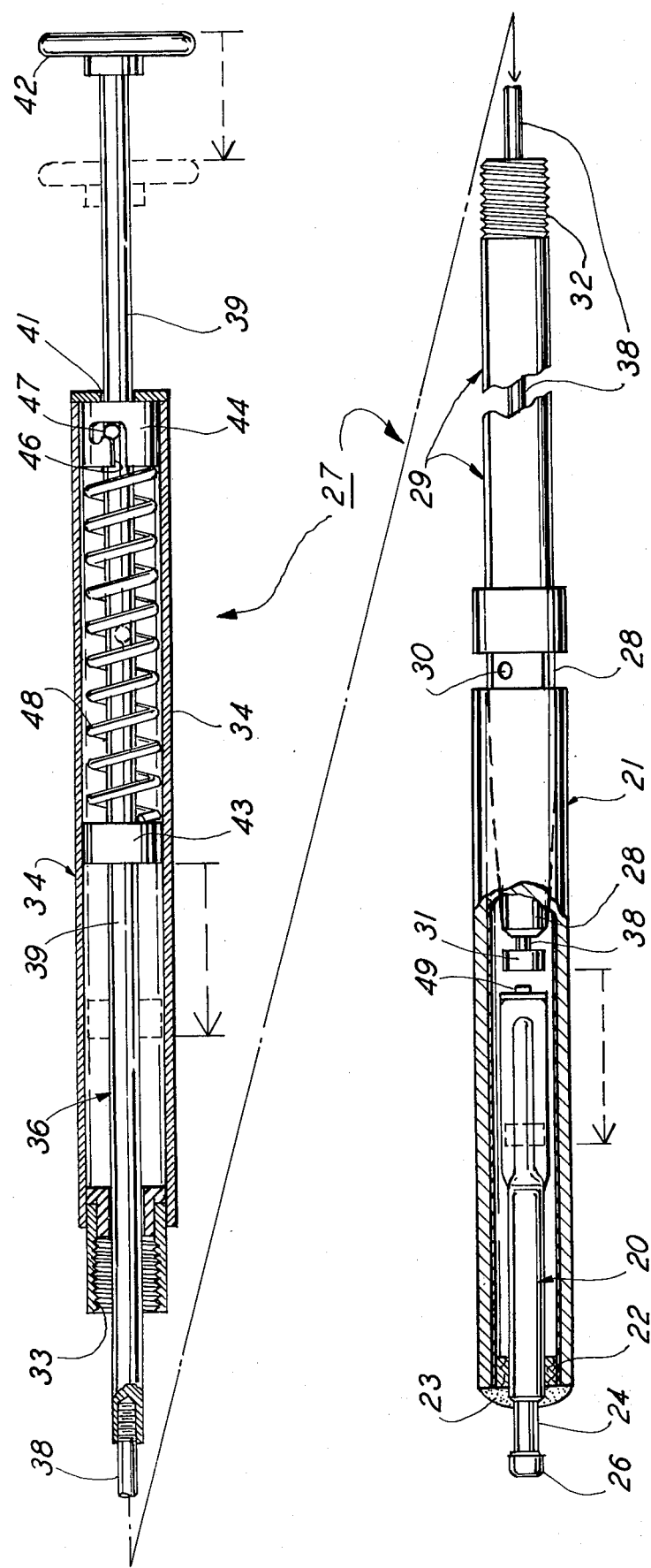
FIG. 3 is an enlarged cross-sectional top plan view of the molten metal sampler and ejector lance assembly of the present invention, showing the ejector mechanism armed or cocked ready for ejection, and indicating the actuated position of the mechanism after ejection.

In these drawings, and in the enlarged cross-sectional view of FIG. 3, the small compact molten metal sampler 20 is mounted at the distal end of the elongated lance tube 21, positioned by such means as an annular spacing ring 22 fitting loosely within the open distal end of the lance tube 21, where it is cemented in position by refractory cement 23. Protruding through cement 23 is a glass or ceramic mold tube 24 whose open distal end is blocked by a sheet metal cap 26 cemented to the inlet portal end of mold tube 24, as best seen in the cross-sectional views of FIGS. 4 and 8.

The lance tube 21 forms the distal end of the combined ejector lance assembly 27 whose internal construction is shown in detail in the cutaway cross-sectional view of FIG. 3.

EJECTOR LANCE ASSEMBLY

Ejector lance assembly 27 combines a substantially conventional lance tube 21, similar to that shown in my U.S. Pat. No. 3,686,949 for example, and incorporating an internal steel tube of heavy gauge steel tubing surrounded by an overlying protective heat insulating layer 41 preferably formed of porous ceramic material like that described in my U.S. Pat. No. 3,561,494. As shown in FIGS. 6 and 7 of my U.S. Patent No. 3,686,949, this lance tube 21 is preferably mounted on a very gently tapered distal end 28 of a portable support tube. In the present invention, this support tube is an ejector tube 29 having a longitudinally movable ejector hammer 31 positioned therein. Vent 30 through tapered portion 28 of ejector tube 29 exposes the interior of lance tube 21 to the atmosphere. The proximal end of ejector tube 29 is preferably provided with external pipe threads 32 designed for threaded engagement with internal pipe threads 33 formed in the distal end of the cylindrical arming tube forming the proximal portion of the overall ejector lance assembly 27.

Thus, as clearly shown in FIGS. 1-3, the three connected parts of the ejector lance assembly 27—the lance tube 21, the ejector tube 29 and the arming tube 34—are formally and rigidly joined together in telescoped colinear relationship to form the greatly elongated rigid lightweight hollow tubular assembly 27 which serves to carry the sampler 20 at its remote distal end into the melt, while its proximal arming tube end 34 is held by the operator's hands 36.

EJECTOR HAMMER ASSEMBLY

Inside the rigidly anchored tubular components forming the continuous ejector lance assembly 27 is a movable ejector hammer assembly 36, which is free for longitudinal reciprocating movement inside the telescoped tubular members forming the ejector lance assembly 27. The movable ejector hammer assembly 36 is formed of hammer 31, anchored to the distal end of hammer shaft 38 whose proximal end is anchored in threaded engagement inside a threaded end bore 37 formed in a reciprocating handle shaft 39 whose proximal end extends through the arming tube 34 and beyond a handle aperture 41 formed in the proximal end of arming tube 34, and terminates in a knob or smoothly rounded disc-shaped handle 42 keyed and firmly anchored to handle shaft 39. At an intermediate point along the length of handle shaft 39 inside arming tube 34 is a radially extending cylindrical spring flange 43. Seated inside the proximal end of arming tube 34 just inside handle aperture 41 is a hollow cylindrical spring collar 44 incorporating a "J-shaped" bayonet socket slot 46, accommodating in free-sliding relationship a bayonet projection 47 extending radially outward from handle shaft 39 into engagement with the J-shaped socket slot 46 in spring collar 44.

Sandwiched between spring flange 43 and spring collar 44 is a helical compression coil spring 48 forming an arming or cocking spring resiliently urging spring flange 43 and thus the entire movable ejector hammer assembly 36 in its distal direction for the ejection and expulsion of samplers 20 from the distal portal end of lance tube 21.

In addition to the compressed spring 48, other actuating mechanisms may be employed if desired. These may include hydraulic and pneumatic piston cylinder actuators, electromagnetic solenoid relays, explosive cartridges or any other desired device suitable for causing the hammer 31 to impact anvil 49 with the desired ejection force.

SAMPLER EJECTION

The movable ejector hammer assembly 36 can be reciprocated between its cocked or armed position shown in solid lines in FIG. 3 to its actuating position shown in dashed lines in FIG. 3. The assembly is easily moved between these two positions by the operator. By holding arming tube 34 in one hand and pulling handle 42 outward in a proximal direction away from the proximal end of arming tube 34, moving handle 42 to the right as shown in FIG. 3, the bayonet projection 47 is brought into the open distal end of socket slot 46 in collar 44. A slight further proximal movement of handle 42 to the right moves bayonet projection 47 down the elongated portion of slot 46, guiding the projection 47 around to the curved or hooked portion of slot 46 into its closed "cul de sac" end. A slight twist on handle 42 clockwise as viewed from the right end of the asembly in FIG. 3 assures the cocking of projection 47 within this closed end of slot 46, bringing spring flange 43 to its closest approach to spring collar 44 and thus compressing the helical coil spring 48 to its shortest compressed length. The energy thus stored in spring 48 is now ready to be released. While the ejector assembly 36 is in this cocked, armed position, the sampler 20 is inserted in an annular or split ring spacer 22 within the open distal end of lance tube 21, and cemented in position by the application of cement 23 as indicated in the lower left-hand portion of FIG. 3, with the mold tube 24 and its sheet metal cap 26 protruding therefrom to form the ultimate distal projecting portion of the overall assembly 27.

In this cocked or armed position of the movable ejector hammer assembly 36, hammer 31 is drawn back in the proximal direction clear of the anvil end 49 of sampler 20, shown in FIG. 3. The sampler and lance assembly is then in the condition illustrated in FIG. 1, ready for immersion sampling by moving the sampler 20 into and beneath the surface of the molten metal in melt 51 contained in a furnace, crucible or other suitable container.

A brief immersion of a few seconds is sufficient to permit the heat of the molten metal 51 to melt sheet metal cap 26, allowing the molten metal to rush into the interior of the mold tube 24 filling the void therein and supplying the sample required. Air displaced from tube 24 by the inflowing molten metal passes through lance tube 21 out vent 30 to the atmosphere. The relatively cool temperature of the mold tube 24 and of the entire sampler 20 as well as lance tube 21 immediately withdraws heat from this molten sample, commencing solidification. As the ejector lance assembly 27 is withdrawn from the melt, this jelling and partial solidification of the sample in sampler 20 prevents the loss of the sample during the remaining few seconds of the sampling operation.

Immediately following its withdrawal from melt 51, the operator moves the ejector lance assembly 27 over to a low temperature fluid chilling bath 52 of liquid nitrogen, ice water or other suitable cold fluid. Aiming the distal end of the assembly 27 toward the bath 52, the operator actuates the assembly 27 by twisting handle 42 in a counterclockwise direction as viewed from the right-hand end of FIG. 3. This slight twisting motion of handle 42 is sufficient to disengage bayonet projection 47 from J-slot 46 in collar 44. The energy stored in the compression coil spring 48 is then released, driving the spring flange 43 briskly to the left in a distal direction.

The entire movable ejector handle assembly 36 is thereby moved longitudinally toward the distal end of the assembly 27, causing hammer 31 to impact sharply on the anvil 49 forming the proximal end of sampler 20. This sharp impact blow shatters cement 23 and drives sampler 20 axially out through the distal portal end of the lance tube 21. As indicated in FIG. 2, the ejected sample 20 travels directly into the chilling bath 52, immediately solidifying the sample contained inside the sampler 20.

The short time consumed by this sampling and chilling operation achieves a unique and highly useful advantage which has been unattainable heretofore by conventional samplers. This advantage is the retention of all or substantially all of the volatile gaseous constituents such as hydrogen contained in the melt 51 during the sampling operation. When the sampling operation consumes a longer period of time, there is rapid diffusion of these entrained gaseous constituents, boiling and bubbling out of the molten sample in response to the reduced pressure to which the sample is exposed. As it is removed from the ferrostatic pressure of the melt 51 and exposed only to atmospheric pressure inside the lance tube 21, this normally permit the escape by diffusion of a substantial portion of such highly volatile gaseous constituents. The rapid sampling collection and ejection illustrated in FIGS. 1 and 2 prevents the loss of most of this volatile gaseous constituent, making the sample recovered inside sampler 20 from the chill bath 52 a highly accurate indicator of the actual volatile gaseous constituents in melt 51 when these constituents are measured and analyzed in spectographic or spectrophotometric analysis of the recovered sample.

COMPACT PIN SAMPLER

The sampler unit 20 cemented in the distal end of the ejector lance assembly 27 is shown in more detail in FIGS. 4–8. In these Figures, it will be seen that the glass or ceramic mold tube 24 is seated in telescoped engagement inside the two halves of a vent tube 53 formed by two shaped vent plates 54 and 56.

The lower vent plate 54 shown in FIGS. 5 and 7 incorporates a distal semi-cylindrical concave portion accommodating mold tube 24 and joined to a substantially flat vent portion 58 having a small central concave grooved channel portion 59 stamped therein. The right hand end forming the proximal termination of vent portion 58 forms the anvil end 49 of the sampler 20.

The upper vent plate 56 illustrated in FIGS. 5, 6 and 7 is very similar to vent plate 54, incorporating a matching semi-cylindrical distal concave portion 61 closely embracing with concave portion 57 of vent plate 54 the external surface of mold tube 24, as indicated in FIG. 4. The upper vent plate 56 likewise incorporates a flat proximal vent plate portion 62 having a small concave channel portion 62 stamped therein, forming with the channel portion 59 of vent plate 54 a cylindrical channel communicating directly with the proximal end of mold tube 24. The proximal end of the flat terminal portion 62 of vent plate 56 is formed with a downwardly extending slotted flange 63 having a central slot 64 accommodating anvil end 49 in telescoping relationship, protruding therethrough as illustrated in FIGS. 4–7. It will also been seen in FIGS. 5 and 7 that an appreciable space remains between the vent plates 54 and 56 in the vent region thereof between the proximal end of mold tube 24 and the anvil 49. This vent space allows the escape of air displaced from mold tube 24 through channel 59–62 by the in-rushing molten metal forming the sample inside sampler 20. The vent tube thus performs the function illustrated in FIGS. 2, 3, 9, 10, 11, 12, 16, 17 and 20 of my my U.S. Pat. No. 4,046,016, as fully explained in the text thereof.

SEPARABLE HINGED VENT PLATES

As shown in FIGS. 4–7, the vent plates 54 and 56 are preferably separably hinged together by the interlocking engagement of anvil 49 in slot 64. Upon ejection from lance tube 21, vent plates 54 and 56 generally separate pivoting about this interconnection 59–64, as shown by dash lines 56A in FIG. 5, and thus releasing the quartz glass mold tube 24 for quick recovery of the sample therein.

DEOXIDANT TREATMENT OF COLLECTED SAMPLE

In the preferred form of the present invention, the sampler 20 is assembled with a deoxidant or "killing" agent in the form of a small body of metal preferably selected from the group consisting of aluminum, titanium or zirconium deployed in the entrace portal of the sampler 20. Thus, as illustrated in FIGS. 4 and 8, a small spring-shaped helically coiled wire of suitable anti-oxidant metal 66 is positioned at the portal end of mold tube 24, directly in front of its entrance portal, and is held in position inside sheet metal cap 26. The usefulness of these antioxidant materials in molten metal sampling is described more fully in my U.S. Pat. No 3,686,949 at Column 8, line 26 through Column 9, line 3.

The coiled wire de-oxidant material 66 preferably has a coil diameter corresponding closely to the diameter of the refractory quartz glass chill mold tube 24, and it is preferably placed directly inside the sheet metal cap 26 and sandwiched between the portal end of the chill mold and the inside of the metal cap, which is then fixed in position on the chill mold tube by a ring of refractory cement 67. It is important that the diameter of the coiled wire de-oxidant material be greater than the internal diameter of the chill mold tube 24, to prevent the wire coils from entering the tube 24 with the inrushing molten metal. The sheet metal cap 26 is preferably surrounded by an external paper cap employed as a slag cover to prevent the contamination of the collected sample by floating slag and the thickness of the metal cap is selected to control the depth of sampling in the molten metal. The outer paper layer is highly effective in slag removal. Upon immersion in the hot floating slag layer, the paper rapidly heats up and vaporizes explosively, blasting away the surrounding slag from the descending sampler and exposing sheet metal cap 26 directly to the molten metal beneath the slag.

De-oxidizing portal chambers have been incorporated in previous samplers for collecting pin samples because of the difficulty of distributing de-oxidant material uniformly through a pin sample. Without such portal chambers to retard and mix the inrushing molten metal, its velocity often sweeps away the de-oxidant material without melting and diffusing it throughout the sampled metal. Examples of such de-oxidizing portal chambers are shown in FIGS. 18B and 20 of my U.S. Pat. No. 4,046,016 and FIGS. 7, 8, 9, 14 and 16 of my U.S. Pat. No. 3,686,949. In these de-oxidizing portal chambers, the inflowing molten metal melts and mixes with the coil or de-oxidant material before it enters the pin sampler mold. Without the use of such an additional portal chamber preceding the pin, it has previously been found impossible to de-oxidize the pin sampler effectively. In the techniques of the present invention, however, the wire coil 66 superimposed around the entrance portal of the chill mold tube 24 performs the desired de-oxidizing function with great effectiveness for many steels of low to moderate oxygen content. Being enclosed inside cap 26, this de-oxidant wire coil is held in position until cap 26 begins to melt. As the center of cap 26 melts and the molten metal rushes through this molten region into the interior of the chill mold tube 24, it flows directly past the interior of the wire coil of de-oxidant material, dissolving and eroding the wire coils and distributing the de-oxidant throughout the inrushing molten metal. Because the wire coil diameter is too large to enter chill mold 24, only portions of the de-oxidant which are dissolved therefrom are available to enter the pin sample collected inside the chill mold tube 24. Normally the rim of the sheet metal cap 26 is the last portion thereof to melt, thus retaining the wire coil de-oxidant in position during the collection of the sample, and the entire sampling procedure takes only a few seconds. The relatively low temperature of the chill mold 24 and lance tube 21 assures that the sample will be sufficiently solidified to remain inside the tube 24 during its withdrawal and ejection into the chill bath 52.

LOW TEMPERATURE MOLTEN METAL SAMPLER

The composition of molten zinc galvanizing baths is a critical factor in maintaining the quality of high volume sheet steel treated in galvanizing lines, like those recently introduced to supply stamping sheet stock for the automobile industry. Sampling must be quick and economical, and the pin samplers of this invention are well adapted to fill this important need.

Figure 9:
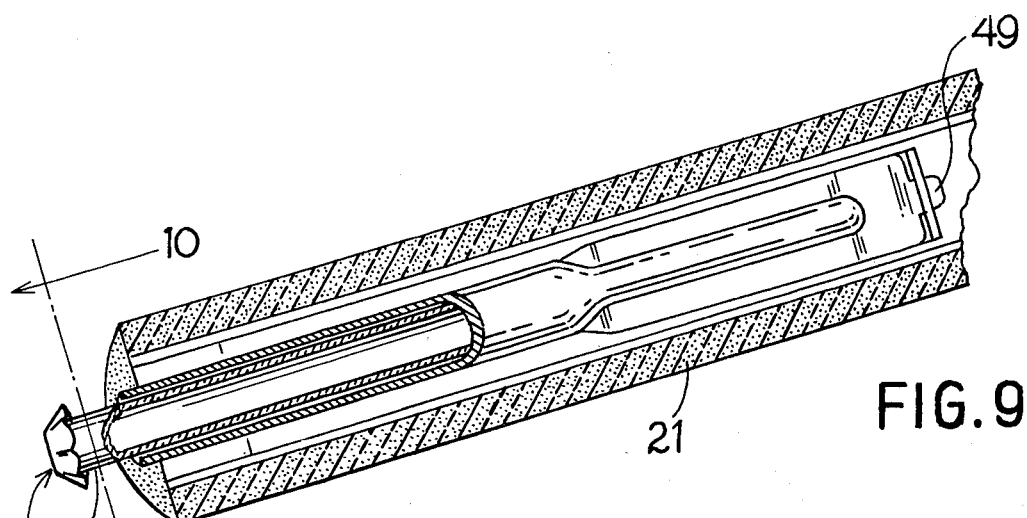
FIG. 9 is a fragmentary cross-sectional side elevation view of a modified sampler for low-temperature molten metals.
Figure 10:
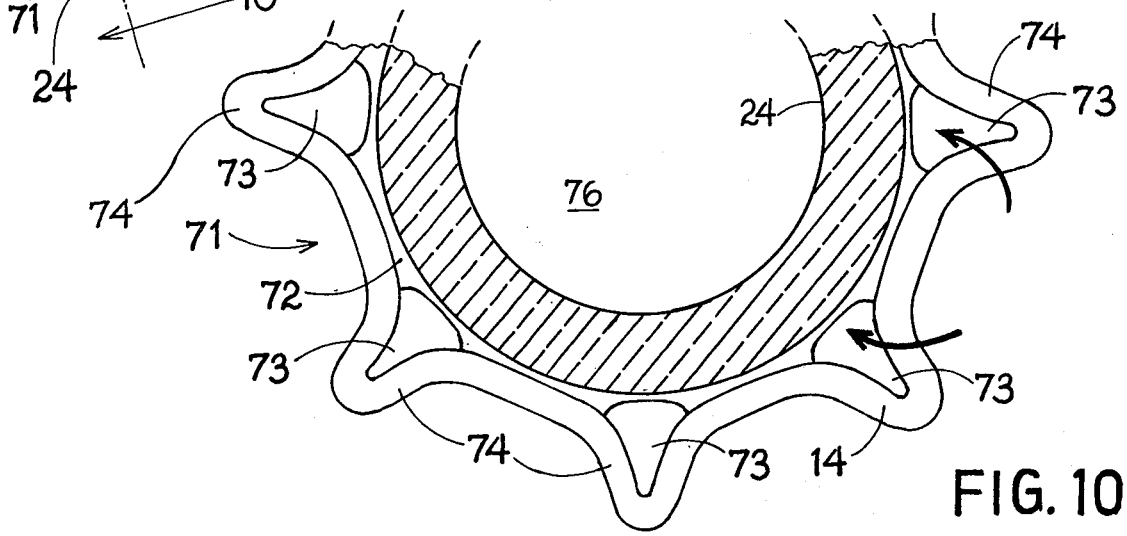
FIG. 10 is a fragmentary greatly enlarged cross-sectional view of the portal end of the sampler of FIG. 9, taken along the line 10—10 in FIG. 9.
Figure 11:
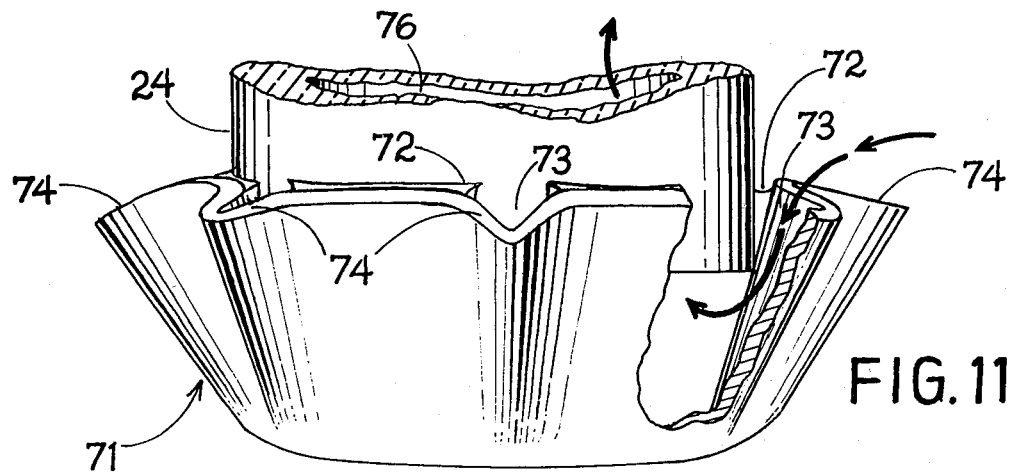
FIG. 11 is a corresponding fragmentary side elevation view of the portal end of the same sampler, partially broken away.

In FIGS. 9, 10 and 11 the quartz glass pin sampler chill mold tube 24 has its entrance portal end capped with a non-ferrous cap 71, preferably of sheet copper, with its rim upturned in a plurality of flutes to form a crown cap similar to a carbonated soft drink bottle cap, but having no cork gasket or comparable sealing member.

Cap 71 embraces the open portal end of tube 24, and is secured thereto by cement patches 72, bonding internal rim sectors of cap 71 between flutes 74 to the juxtaposed outer rim sections of tube 24 leaving openings 73 in most or all of the flutes 74 connecting the interior pin-shaped chill mold cavity 76 inside tube 24 with the outside atmosphere.

Cap 71 provides the same slag, "kish" or scum diverting action as does cap 26 in FIGS. 5, 6 and 8, as the sampler-lance tube assembly of FIG. 9 is plunged endwise beneath the surface of molten zinc in a galvanizing bath having a temperature between 750° F. and 900° F. Once immersed beneath any floating debris, the openings 73 inside each flute 74 provide free access conduits for molten zinc, driven by its own fluid pressure head, to enter and flow into chamber 76 inside chill tube 24.

A few seconds immersion is sufficient to collect and chill a pin sample to a slush temperature low enough to retain it in the sampler during withdrawal from the galvanizing bath, preventing the sampled zinc from draining out as the sampler-lance assembly is withdrawn from the bath, provided the sampler does not remain immersed long enough to heat the sampler and re-melt the pin sample therein.

Since ferrous contamination of the zinc is the impurity being measured, to assure optimum galvanizing adhesion to the underlying steel workpiece or sheet, a steel cap 71 would permit erosion of ferrous particles into the inrushing molten zinc, reducing the reliability of the constituent analysis of the sample. A copper cap 71 avoids this additional source of contamination, and any copper traces found in the sampled metal can be disregarded during spectrographic anlysis.

It will thus be seen that the objects set forth above, among those made apparent from the preceding description, are efficiently attained and, since certain changes may be made in the above constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

I claim:

1. A molten metal sampler assembly comprising an elongated, open-ended heat-insulated lance tube,
   a hollow cylindrical heat-resistant chill mold tube sampler secured in slidably removable engagement near a first open distal end of the lance tube and having a distal entrance portal end and a proximal vent portal end,
   and elongated longitudinally reciprocable ejector means telescopingly extending into the second proximal open end of the lance tube for ejection-impact contact with the sampler producing sliding disengagement and longitudinal ejection of the sampler from the first distal end of the lance tube, whereby the chill mold tube sampler may be immersed in a body of molten metal to collect a melt sample inside the chill mold tube, and then withdrawn and aimed at a chilling fluid bath, and the ejector means may then impact the sampler to eject the sampler and the melt sample contained therein into the chilling fluid bath.

2. A molten metal sampler assembly comprising
   an elongated, open-ended heat-insulated lance tube,
   a hollow cylindrical heat-resistant chill mold tube sampler secured in slidably removable engagement near a first open distal end of the lance tube and having a distal entrance portal end and a proximal vent portal end,
   means forming an elongated heat-resistant hollow riser vent secured to the chill mold tube and having an internal channel connecting the vent portal via vent slot means to the space outside the riser vent inside the lance tube,
   and elongated longitudinally reciprocable ejector means telescopingly extending into the second proximal open end of the lance tube for ejection-impact contact with the riser vent producing sliding disengagement and longitudinal ejection of the riser vent and the chill mold tube from the first distal end of the lance tube,
   whereby the lance tube with the chill mold tube secured therein may be partially immersed in a body of molten metal to collect a melt sample inside the chill mold tube, and then withdrawn and aimed at a chilling fluid bath, and the ejector means may then impact the riser vent to eject the chill mold tube and the melt sample contained therein into the chilling fluid bath.

3. The sampler assembly defined in claim 2, wherein the riser vent incorporates a projecting proximal end forming an anvil facing the ejector means inside the lance tube, and wherein the ejector means incorporates a distal hammer end facing the anvil inside the lance tube.

4. The sampler assembly defined in claim 2, wherein the lance tube is mounted telescopingly on an elongated hollow ejector tube within which the ejector means is reciprocably mounted.

5. The sampler assembly defined in claim 2, wherein the ejector means is connected to means forming an arming device for actuating the ejector means to move it from an armed position to an ejection position producing said ejection-impact contact.

6. The sampler assembly defined in claim 5, wherein the arming device incorporates a resilient compression spring connected to be retracted into a compressed "armed" condition from which it is actuated to release the compressed spring and thereby produce the ejection-impact force.

7. The sampler assembly defined in claim 2, wherein the hollow riser vent means is formed by two mating vent plates concavely shaped for embracing the chill mold tube and having separably interlocked proximal ends defining the vent slot means therebetween, whereby upon ejection from the lance tube the vent plates are free to separate and release the chill mold tube.

8. A molten metal sampler assembly comprising
   a hollow cylindrical heat-resistant chill mold tube secured in slidably removable engagement near a first open distal end of an elongated lance tube and having a distal entrance portal end and a proximal vent portal end, means forming an elongated heat-resistant hollow riser vent secured to the chill mold tube and having an internal channel connecting the vent portal via vent slot means to the space outside the riser vent, a thin cup-shaped sheet metal cap telescopically embracing and covering the distal entrance portal end of the chill mold tube, and a circular wire coil of metallic de-oxidant material positioned inside the sheet metal cap, between the cap and the portal end of the chill mold tube, whereby immersion of the chill mold tube beneath the surface of a body of molten metal heats the cap causing the cap to melt at a predetermined depth in the molten metal, which flows past the de-oxidant wire coil into the entrance portal, filling the chill mold tube with a de-oxidized sample of molten metal having de-oxidant from the coil dissolved substantially uniformly therein.

9. A molten metal sampler assembly comprising a hollow cylindrical heat-resistant chill mold tube secured in slidably removable engagement near a first open distal end of an elongated lance tube and having a distal entrance portal end and a proximal vent portal end, means forming an elongated heat-resistant hollow riser vent secured to the chill mold tube and having an internal channel connecting the vent portal via vent slot means to the space outside the riser vent, a thin cup-shaped paper-covered sheet metal cap telescopically embracing and covering the distal entrance portal end of the chill mold tube and secured thereto by refractory cement, and a circular wire coil of metallic de-oxidant material selected from the group consisting of aluminum, titanium and zirconium, having a coil diameter substantially the same as the chill mold tube diameter, positioned inside the sheet metal cap, between the cap and the portal end of the chill mold tube, whereby immersion of the chill mold tube beneath the surface of a body of molten metal heats the paper-covered cap while it descends through any accumulated hot floating slag, causing the paper covering to vaporize and deflect slag therefrom, permitting the metal cap to melt after it has descended through such slag into molten metal, which flows past the de-oxidant wire coil into the entrance portal, filling the chill mold tube with a de-oxidized sample of molten metal having de-oxidant from the coil dissolved substantially uniformly therein.

10. A molten metal sampler assembly comprising a hollow cylindrical heat-resistant chill mold tube secured in slidably removable engagement near a first open distal end of an elongated lance tube and having a distal capped entrance portal end and a proximal open vent portal end, and means forming an elongated heat-resistant hollow riser vent secured to the chill mold tube and having an internal channel connecting the vent portal via vent slot means to the space outside the riser vent, with the hollow riser vent being formed by a pair of elongated concave vent plates separably hingedly connected together and defining the vent slot means between adjoining edges thereof, whereby immersion of the chill mold tube beneath the surface of a body of molten metal permits the molten metal to flow into the entrance portal, filling the chill mold tube with a solidified sample of molten metal, and whereby removal of the chill mold tube from the lance tube releases the separably connected vent plates from the chill mold tube for quick recovery of a metal sample collected inside the chill mold tube.

11. A pin sampler for immersion in a molten metal bath of a first metal incorporating an elongated cylindrical ceramic chill mold tube having a distal entrance portal end and a proximal exit portal end, a metal riser vent embracing and partially blocking the exit portal end of the chill mold tube and having slot means providing an escape vent for air displaced from the tube by molten metal entering the entrance portal end of the tube, a fluted crown cap formed from a sheet of a second metal whose melting point is substantially higher than the melting point of the first metal, embracing and partially blocking the entrance portal end of the tube, and having internal rim sectors between flutes adhesively bonded to the juxtaposed outer entrance portal rim portions of the chill mold tube, with each of the flutes enclosing between itself and the chill mold tube rim a conduit connecting the interior of the chill mold tube to the space outside the crown cap, and a porous ceramic lance tube insulatingly embracing the riser vent and the chill mold tube with its crown cap covered entrance portal end exposed protruding from one end of the lance tube, whereby plunging endwise immersion of the exposed sampler entrance portal end and the embracing end portion of the lance tube beneath the surface of a bath of the molten first metal causes said molten metal driven by fluid pressure to flow quickly through the flute conduits into the interior of the chill mold tube, displacing air therefrom through the riser vent slot means into the interior of the lance tube.

* * * * *